United States Patent
Blau et al.

(10) Patent No.: US 7,763,030 B2
(45) Date of Patent: Jul. 27, 2010

(54) DEVICE AND METHOD FOR CALIBRATING AN ELEMENT AND DEVICE AND SYSTEM FOR POSITIONING AN ELEMENT

(75) Inventors: Arno Blau, Schwyz (CH); Falko Seifferth, Zorneding (DE); Mario Zeiss, Tokyo (JP)

(73) Assignee: BrainLAB AG, Kirchheim/Heimstetten (DE)

( * ) Notice: Subject to any disclaimer, the term of this patent is extended or adjusted under 35 U.S.C. 154(b) by 886 days.

(21) Appl. No.: 10/692,023

(22) Filed: Oct. 22, 2003

(65) Prior Publication Data

US 2004/0158260 A1 Aug. 12, 2004

Related U.S. Application Data

(60) Provisional application No. 60/440,703, filed on Jan. 17, 2003, provisional application No. 60/440,707, filed on Jan. 13, 2003.

(30) Foreign Application Priority Data

Oct. 25, 2002 (EP) .................................. 02023790
Oct. 25, 2002 (EP) .................................. 02023791

(51) Int. Cl.
*A61B 17/88* (2006.01)
(52) U.S. Cl. ....................................................... 606/99
(58) Field of Classification Search ............... 606/61, 606/97, 99, 104, 130, 102, 86 R, 86 A, 246
See application file for complete search history.

(56) References Cited

U.S. PATENT DOCUMENTS

| 2,329,398 | A | | 9/1943 | Duffy | |
|---|---|---|---|---|---|
| 4,305,394 | A | * | 12/1981 | Bertuch, Jr. .................. | 606/91 |
| 5,320,625 | A | * | 6/1994 | Bertin .......................... | 606/91 |
| 5,662,657 | A | * | 9/1997 | Carn ........................... | 606/95 |
| 5,855,579 | A | | 1/1999 | James et al. | |
| 6,226,548 | B1 | | 5/2001 | Foley et al. | |
| 6,351,659 | B1 | | 2/2002 | Vilsmeier | |
| 6,416,518 | B1 | | 7/2002 | DeMayo | |

FOREIGN PATENT DOCUMENTS

DE 196 39 615.8 4/1998

* cited by examiner

*Primary Examiner*—Eduardo C Robert
*Assistant Examiner*—David Comstock
(74) *Attorney, Agent, or Firm*—Renner, Otto, Boisselle and Sklar, LLP

(57) ABSTRACT

A system for positioning an implant includes a holding element for holding an implant. The holding element can include a first end having a grip and a second end having a connecting element for establishing a connection to the implant. The system includes a guiding sleeve for guiding the holding element. The guiding sleeve defines a guiding area for guiding the holding element, where the holding element can be introduced into the guiding sleeve and a method for calibrating an element includes connecting the element to at least one navigation element and placing the element in contact with a calibrating device. The element is moved while the element remains in contact with the calibrating device. A device for calibrating an element includes a planar member connected to at least one navigation element.

12 Claims, 3 Drawing Sheets

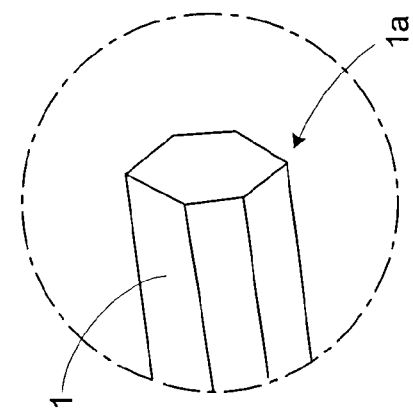
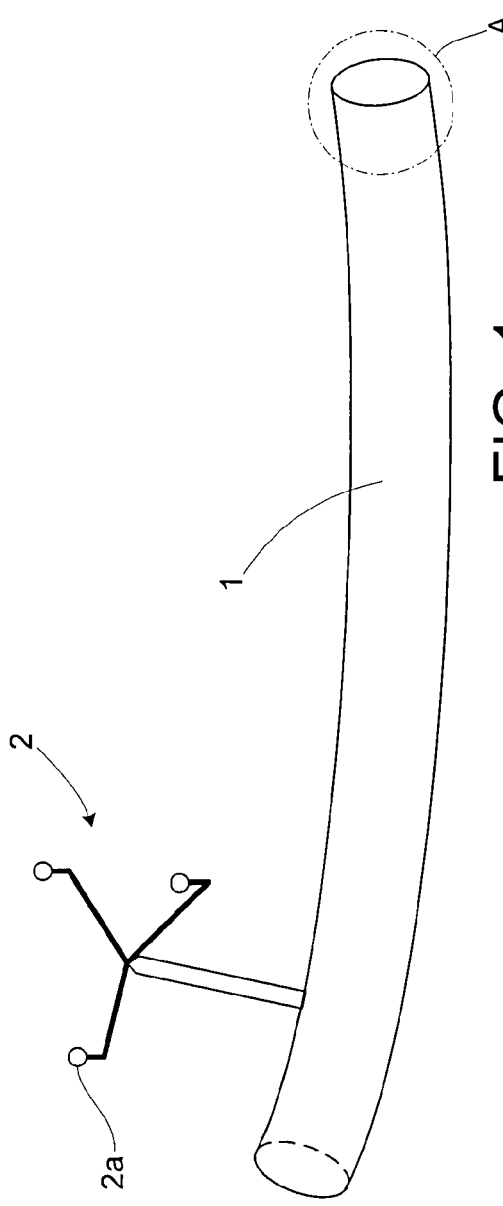
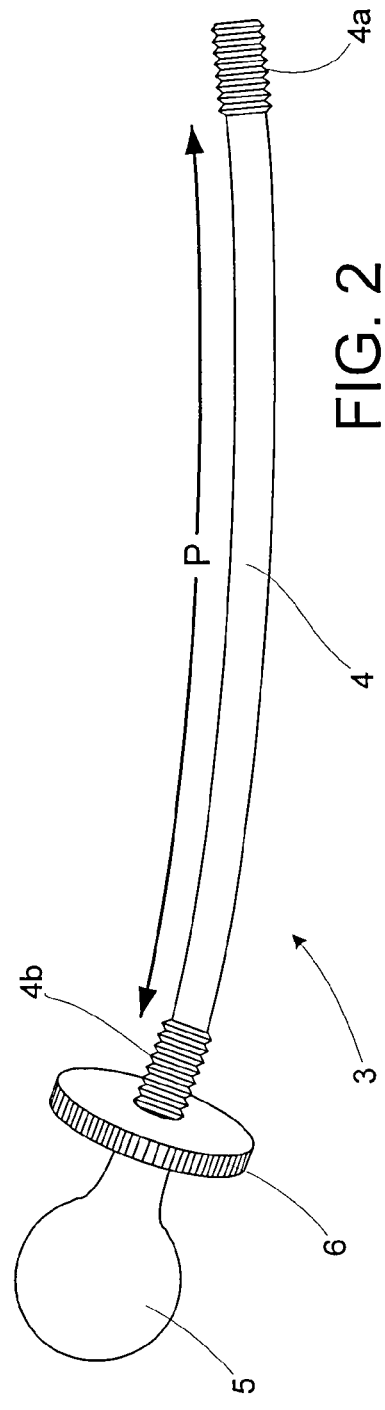

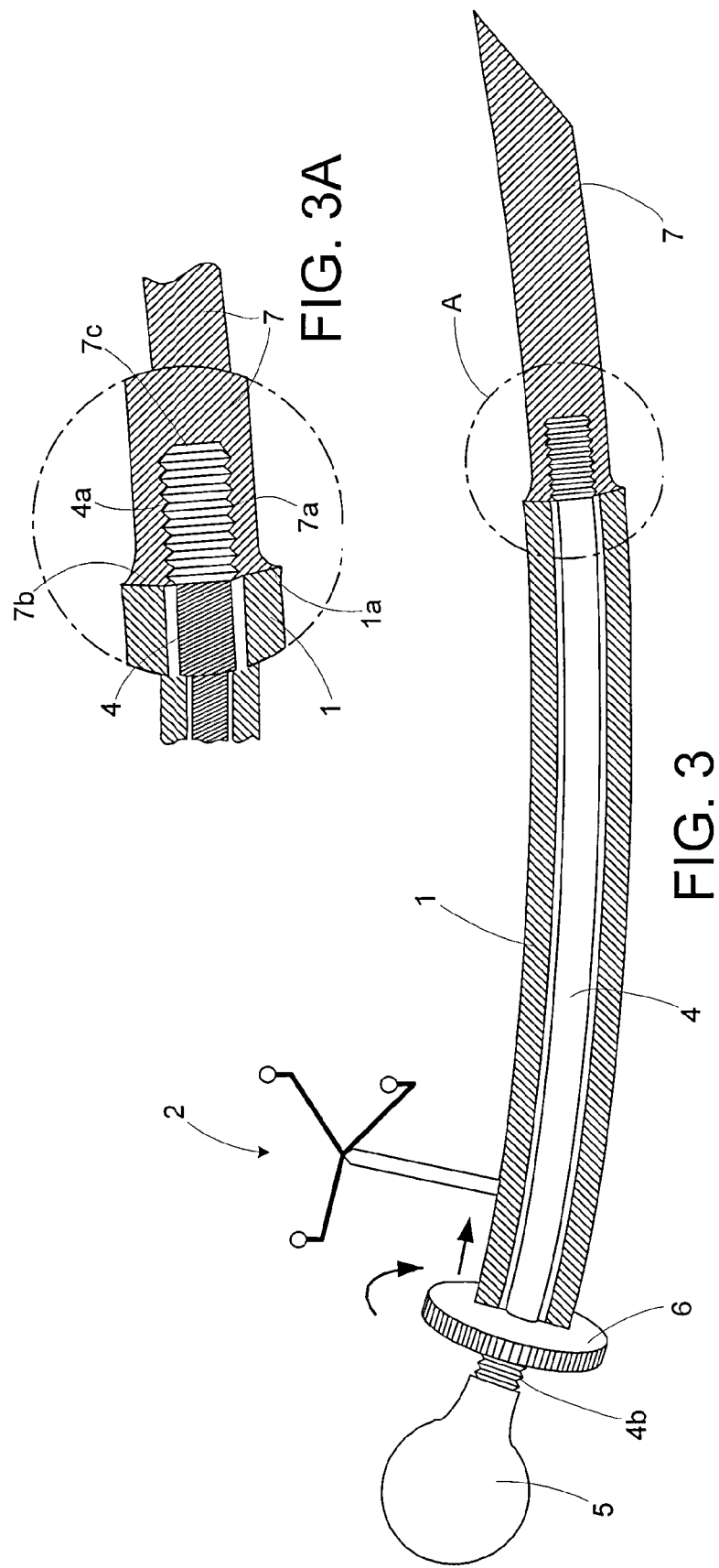

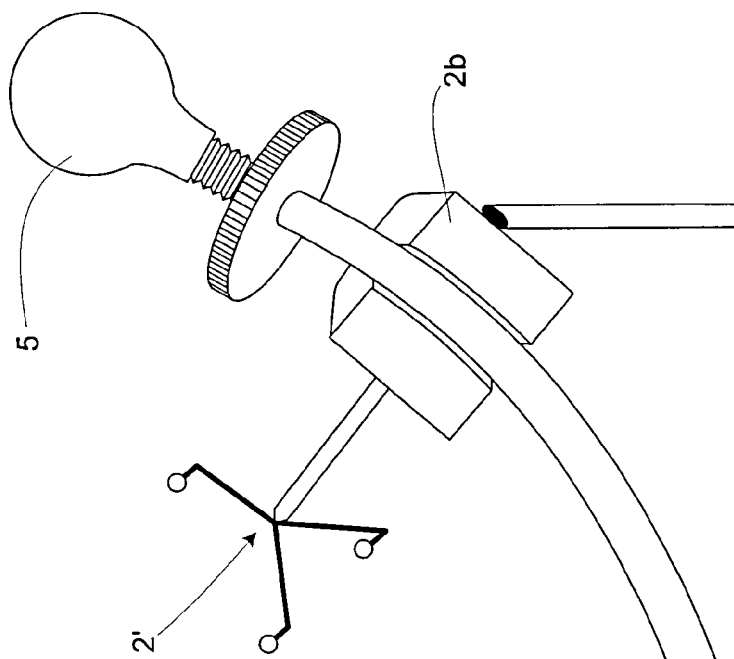
FIG. 4
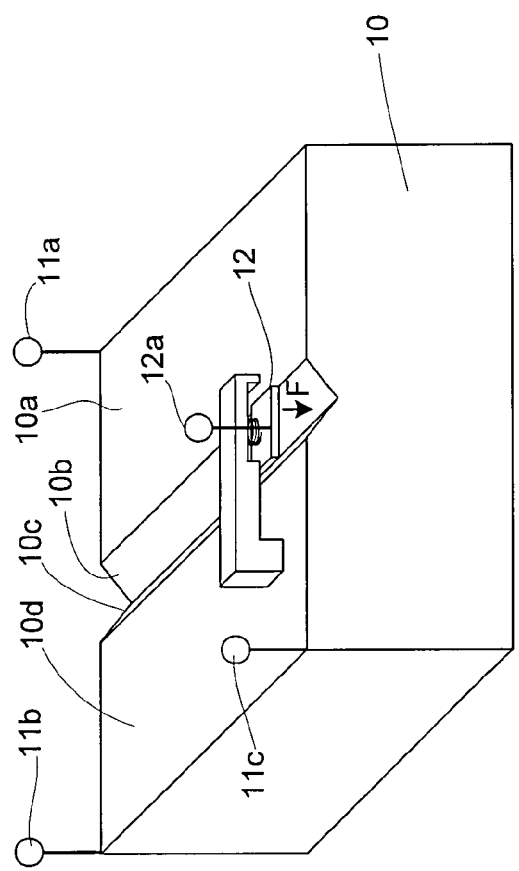
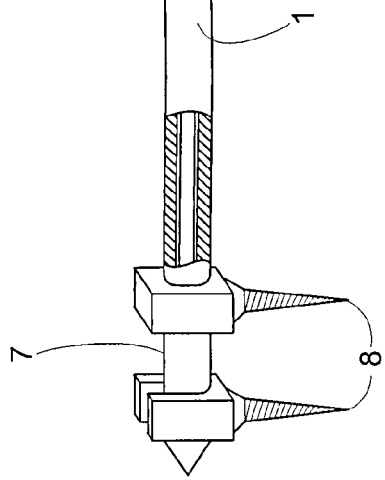
FIG. 5

DEVICE AND METHOD FOR CALIBRATING AN ELEMENT AND DEVICE AND SYSTEM FOR POSITIONING AN ELEMENT

RELATED APPLICATION DATA

This application claims priority of U.S. Provisional Application No. 60/440,703, filed on Jan. 17, 2003 and of U.S. Provisional Application No. 60/440,707, filed on Jan. 13, 2003, which are incorporated herein by reference in their entirety.

FIELD OF THE INVENTION

The present invention relates generally to a device for inserting an element, such as a rod, into a body in a minimally invasive way. The invention further relates generally to a method for calibrating an element, such as a curved implant or instrument, which can be used in operations in the area of the spine.

BACKGROUND OF THE INVENTION

During surgery or operations in the area of the spine, such as operations involving attaching pedical screws to individual vertebrae and fixing rods between pedical screws on adjacent vertebrae, the entire area of the spine to be operated on is exposed. First, the pedical screws are inserted into the exposed vertebrae, then each rod is placed between two pedical screws on adjacent vertebrae and connected to them using screws. The open tissue is then closed over the inserted pedical screws and the rods connected to them again. Accordingly, such surgery in the area of the spine requires the tissue to be opened in a relatively large area.

A pedical screw including a device arranged on it for fixing a rod is known from U.S. Pat. No. 6,371,957 B1, which is incorporated herein by reference in its entirety.

Opening a relatively large area of tissue, however, causes problems including an increased risk of infection or complications as the corresponding area heals. Furthermore, scars may be present after such surgery, which is undesirable for aesthetic reasons.

SUMMARY OF THE INVENTION

According to one aspect, the invention relates to a method for calibrating an element, such as a curved implant or instrument, e.g., a surgical instrument, which can be used in operations in the area of the spine. According to another aspect of the invention, the invention relates to a device for inserting an element, such as, for example, a rod, into a body in a minimally invasive way. The element can be moved to a particular position using a navigation method and connected using pedical screws, during surgery in the area of the spine.

According to one aspect of the invention, the invention relates to a method for calibrating a, for example, curved or rotationally asymmetrical element or instrument, such as, for example, an implant, a guiding sleeve and/or a holding element. The element or instrument can be connected to at least one navigation element and can contact a calibrating device in at least two or more different positions. The calibrating device can include one or more surfaces whose trajectory or spatial position is known. The calibrating device can, for example, be a plane whose spatial position is known.

First, the spatial position of the element or instrument can be ascertained at least one point connected to the at least one navigation element. If the element or instrument is placed on the plane and moved or rotated over the plane, such that the element or instrument always lies on the plane via at least one point; then a plurality of readings can be ascertained. From these readings, the trajectory of the curved element or instrument and/or its geometry can be ascertained, given a sufficiently large number of different contact positions. Mathematically, the trajectory or the geometry of the element or instrument can be regarded as the entire three-dimensional space prior to calibration. Each detected reading, which represents a particular contact position of the element or instrument on the known plane, can be seen as narrowing the possibilities for the three-dimensional trajectory of the element or instrument to be calibrated. In principle, a detected reading in a particular contact position of the instrument or element relative to a contact plane can be interpreted in such a way that the contact plane is a tangential plane on the instrument or element to be calibrated and this tangential plane is the interface of a half-space, which is excluded as the trajectory of the instrument or element and can, therefore, be cut away from the originally available three-dimensional space. If a number of contact positions of the instrument or element on the plane are detected, then a number of partial spaces can be cut out of the originally available three-dimensional space, such that after a sufficiently large number of readings or contact positions, the spatial trajectory of the curved element or instrument can be ascertained.

The term "calibrate" is intended to mean determining the geometry or the spatial trajectory of a body generally, such as, for example, an instrument or element.

A plausibility check can be performed in combination with the method described below, if, for example, particular assumptions with respect to the geometry or the spatial trajectory of the instrument or element to be calibrated can be taken into account during the calibrating method. These assumptions or information can either be fixedly set or predetermined by a user. For example, it can be assumed that the element or instrument to be calibrated does not exhibit a flaw, that it has a substantially constant, known or still to be determined diameter, that it is only curved in one direction, etc.

In one embodiment, the tip of an instrument or element to be calibrated can be calibrated in a known way before the calibrating method is performed, i.e., in addition to the point of the instrument or element to be calibrated, which is connected to the navigation element, the spatial position of another point of the instrument or element to be calibrated is known, thus simplifying the calibrating method. The tip can be calibrated, for example, by moving the tip to a spatial position, which is known.

The shape of the element to be calibrated, which can be ascertained from the data or positions detected up until then, can be displayed during the calibrating method, such that it is possible to check whether the correct shape of the instrument or element is in principle being detected, or whether an error has occurred during calibration.

The invention further relates to a device for calibrating an element or instrument, such as a curved element or instrument. At least one navigation element, such as, for example, a reference star of two, three or more markers, can be attached to the device, such that the spatial position of the device for calibrating can be detected.

The device can, for example, include a plane surface, which the instrument or element to be calibrated can contact. Alternatively, the device can include two or more adjacent planes forming, for example, an edge or a V-shape. The element or instrument to be calibrated can then be inserted into the V formed by the planes, such that it has at least one point of contact with each of the planes forming the V, thus simplifying the calibrating method.

The device for calibrating an instrument or element can include a movable element, which is connected to the device and can be moved, for example tilted or pivoted, relative to the device. The movable element is connected to at least one marker or navigation element. The movable element can be arranged in such a way that it can have contact with at least one other point of the element or instrument to be calibrated and which is lying on the device, thus further improving the calibration of the instrument. The movable element can, for example, be arranged in such a way that it exerts a pressure force in the direction of the calibrating device via a spring or its own weight. This brings the element or instrument to be calibrated, and which contacts the device, into contact with the movable element pressing in the direction of the device, on a side facing away from the device. This enables an element or instrument to be calibrated more quickly and more precisely.

The position of the movable element, biased, for example, by a spring, or of a spring element, can be ascertained by a marker arranged on it and tracked in the vertical direction. Mathematically, it may be assumed that a cuboid, extending infinitely upwards, infinitely perpendicular to the V-groove (for example parallel to the surface of the calibrating device), and parallel to the V-groove by the width (parallel to the V-groove) of the spring element, exists above the spring element, which is pressed onto the element to be calibrated (instrument or implant) by a force F. The cuboid can be separated from the otherwise remaining space, which is regarded as belonging to the instrument or implant. That is to say, the space available for the geometry of the instrument to be calibrated is reduced by the cuboid thus generated.

The calibrating process can, for example, be restricted in time, such that after a start time, data is only collected over a predetermined period of time. The instrument or element to be calibrated should always be contacting the calibrating device, i.e., should always have at least one point of contact, during calibration, and it should be rotated, for example, by at least 180°. If a sufficient amount of data for specifying the geometry of the instrument or element, corresponding to a minimum angular range or a minimum rotational range, has been collected during calibration, then the geometry or the spatial trajectory of the instrument or element can be determined, thus calibrating said instrument or element.

If the element or instrument to be calibrated exhibits a simple geometry, i.e., the instrument is, for example, a straight rod, then the method for calibrating the instrument is relatively simple to perform, since the rod merely has to be placed onto a planar calibrating device and rotated about its longitudinal axis. The spatial trajectory of the rod relative to the navigation element connected to the rod is already known. Instruments or elements having a more complicated structure have to be moved in a number of positions in contact with the calibrating device, in order to be able to describe their geometry with sufficient precision.

The invention further relates to a computer program which, when it is loaded onto a computer or is running on a computer, performs at least one of the method steps described in this application, and to a program memory medium comprising such a computer program.

According to one aspect of the invention, the invention relates to a device for inserting an element, such as, for example, a rod, into a body in a minimally invasive way. The element can be moved to a particular position using a navigation method and connected using pedical screws, during surgery in the area of the spine. According to another aspect, the invention relates to a method for calibrating an element, such as a curved implant or instrument, e.g., a surgical instrument, which can be used in operations in the area of the spine.

In accordance with one aspect of the invention, a guiding sleeve, which may, for example, be used to guide a holding element described below, includes an entry opening and an exit opening through which a holding element can be slid or otherwise translated. A guiding area lies between the entry opening and the exit opening, such that the holding element can be guided in the area such that the holding element can be slid through the guiding sleeve and, for example, rotated in it. In one embodiment, the guiding sleeve can be an annular or tubular element, running in a straight line or curved, through which the holding element can be slid and guided. The guiding sleeve is preferably rigid, such that it cannot easily be deformed and it is, therefore, ensured that the holding element is securely and precisely guided. The guiding sleeve can, also be made of an elastic material or a combination of elastic and rigid sections, in order to be able to change the shape of the guiding sleeve and adapt it to a particular application. Thus, an elastic or ductile material used for the guiding sleeve should exhibit a certain resistance to being deformed by external forces, in order to prevent the guiding sleeve from being unintentionally deformed and, therefore, the holding element from being guided to an undesired position.

The guiding sleeve can be curved or exhibit at least one curved or arched section.

A fixing area for a navigation element, such as, for example, a reference star or other combination of one or more active or passive markers, can be provided on the guiding sleeve. The use of navigation elements, such as, for example, markers for navigating and positioning instruments, is described more fully in commonly assigned U.S. Pat. No. 6,351,659, which is incorporated herein by reference in its entirety. A guiding sleeve connected to a navigation element enables a holding element guided in the guiding sleeve and/or another element connected to the holding element, such as, for example, a rod, which can be positioned between two, three or more pedical screws, to be navigated.

A navigation element, such as a reference star, can be slid onto the guiding sleeve using a sliding element, such that the guiding sleeve can be moved relative to the navigation element. The guiding sleeve can then be slid through a sliding element connected to a navigation element and held in a broadly stable position, such that given a known, constant curvature of the guiding sleeve, an element guided by the guiding sleeve can be positioned at a predetermined desired point.

In one embodiment, the end of the guiding sleeve, which is to come to rest on an element to be positioned, such as for example, an implant or rod, exhibits a geometry and/or surface which impedes or prevents the element to be positioned from slipping. One end of the guiding sleeve can be formed tapering conically outwards or inwards, in order, along with a correspondingly formed end of an element to be positioned, to ensure that the element is held. A rotational block, such as, for example, a structured surface or protruding elements, can be provided in the contact area with an implant, in order to be able to hold it securely and to move it.

Furthermore, a holding element can be provided. The holding element can be guided, for example, by the guiding sleeve described above and, for example, slid through and rotated in the guiding sleeve. The holding element can include a connecting element, which can be connected to an element to be positioned, such as, for example, an implant or a rod, or which can hold the element to be positioned, for example, in a frictional lock or by clamping.

In accordance with one embodiment, the holding element can include at least one rigid and/or flexible or bending area and is, for example, a rod which can be rigid or flexible and is in particular suitable for guiding through the guiding sleeve. Such a rod can have an outer diameter, which is slightly smaller than the inner diameter of the guiding sleeve, in order to ensure that the rod is easily slid through the guiding sleeve.

The connecting element provided for connecting the holding element to an element to be positioned can be an external thread or an internal thread, which can mesh with a corresponding internal or external thread of the element to be guided, so as to establish a connection with the element. In this case, it can be advantageous to design the holding element and the guiding sleeve such that the holding element can not only be shifted, but also rotated in the guiding sleeve.

The holding element can include a grip and/or a thread on the end opposite the end for holding the element to be positioned. A nut or other suitable fastening element can be screwed onto the grip or thread, in order to be able to fix the holding element, inserted into the guiding sleeve, relative to the guiding sleeve by clamping the guiding sleeve between two areas or between the ends of the holding element. Alternatively or in addition, other holding mechanisms, such as, for example, clamps, can also be provided on the holding element and/or on the guiding sleeve, in order to enable the holding element to be fixed relative to the guiding sleeve.

In accordance with another aspect of the invention, an element to be positioned, such as, for example, an implant or a rod, which is to be positioned between two pedical screws, includes at least one connecting element, which can cooperate with a corresponding connecting element on the holding element, in order to connect the element to be positioned to the holding element. The connecting element can, for example, be an internal or external thread.

The element to be positioned can be formed conically tapering or pointed at the end opposite the end of the element at which the connecting element is provided, such that the tip or a conically tapering area simplifies inserting the element to be positioned into a body.

In the area of the connecting element, the element to be positioned can be designed such that it can be held as nonshifting as possible by a holding element and/or a guiding sleeve. This can, for example, be an area of the element to be positioned, which conically tapers outwards or inwards.

In accordance with another aspect, the invention relates to a system including a guiding sleeve, as described above, and a holding element, as described above. The system can further include an element to be positioned, as described above, wherein the holding element can preferably be slid through the guiding sleeve and connected to the element to be positioned.

Such a system enables an element or implant to be positioned precisely, using navigation and in a minimally invasive way. The element or implant can be inserted into a body through a relatively small opening through the tissue and positioned at a desired point in the body using the navigation element connected to the guiding sleeve and/or the holding element. Both the holding element and the guiding sleeve can be removed again from the body, once the connection between the holding element and/or the guiding sleeve, on the one hand, and the implant or element to be navigated, such as a rod, on the other, has been released.

BRIEF DESCRIPTION OF THE DRAWINGS

These and further features of the present invention will be apparent with reference to the following description and drawings, wherein:

FIG. 1 is a perspective view of a guiding sleeve in accordance with the invention;

FIG. 1A is an enlarged detail view of the front end of the guiding sleeve shown in FIG. 1;

FIG. 2 one embodiment of a holding element in accordance with the invention;

FIG. 3 is a perspective view of a system for positioning an element or implant in accordance with one embodiment of the invention;

FIG. 3A is an enlarged cross-sectional view of the cutaway A shown in FIG. 3;

FIG. 4 is a perspective view of a system for positioning an element or implant in accordance with an alternative embodiment of the invention; and FIG. 5 is a perspective view of a calibrating device in accordance with the invention.

DETAILED DESCRIPTION OF THE INVENTION

FIG. 1 shows a tubular guiding sleeve 1, which is connected to a reference star 2 (also referred to as a navigation star) including three passive markers 2a. The guiding sleeve 1 is open at its rear end, (shown on the left in FIG. 1), and at its front end, (shown on the right in FIG. 1). FIG. 1A shows a cross-section of the part of the guiding sleeve 1 indicated by A in FIG. 1, in an enlarged representation. As shown in FIG. 1A, the guiding sleeve 1 includes a rim area 1a which runs broadly conically, onto which an implant 7 can be placed, as shown in FIG. 3.

FIG. 2 shows a holding element 3. The holding element 3 can include an elastic or otherwise flexible section 4 (shown by the arrows P). The section 4 can, for example, be a flexible metal or plastic element having an outer thread 4a in its front end, (shown on the right in FIG. 2). The rear end of the flexible section or area 4, (shown on the left in FIG. 2), likewise can include an outer thread 4b, onto which a nut 6 or other fastening mechanism is screwed or otherwise attached. A grip 5 is connected to the outer thread 4b. The grip 5 can serve to hold the holding element 3.

FIG. 3 shows the holding element 3 shown in FIG. 2, inserted into the guiding sleeve 1 of FIG. 1, where the flexible area 4 has been guided through the guiding sleeve 1. The front end of the implant 7 is screwed onto the front outer thread 4a of the holding element 3, as shown.

FIG. 3A shows an enlarged cross-sectional view of the part from FIG. 3 indicated by A. The implant 7 can be tapered at its front end, shown on the right, and can include an inner thread 7a at its rear end. The implant 7 can be screwed or otherwise fastened onto the outer thread 4a of the flexible part 4 of the holding element 3 via said inner thread 7a. Furthermore, the rear end of the implant 7 is conically tapered in the area 7b and therefore contacts the corresponding conical rim area 1a of the guiding sleeve 1.

In order to provide the system shown in FIG. 3, the nut 6 should be screwed on the outer area of the outer thread 4b in the direction of the grip 5, as shown in FIG. 2. The holding element 3 can be inserted into the guiding sleeve 1. In this position, the implant 7 can be screwed onto the front outer thread 4a, preferably until it abuts the front area of the flexible element 4 at the inner boundary 7c of the implant 7. The nut 6 can then be screwed in the direction of the implant 7 until the guiding sleeve 1 is securely tensed between the nut 6 and the implant 7, connected to the holding element 3, such that the individual components of the system shown in FIG. 3 can substantially no longer slip relative to each other.

The system thus composed can then be navigated either using a reference star 2, fixedly connected to the guiding sleeve 1, or, alternatively, using a reference star 2' attached via a shifting element 2b, as shown in FIG. 4. The shifting element 2b can, for example, then be held in such a way that the guiding sleeve 1 can be moved through the shifting element 2b such that the implant 7 connected to the guiding sleeve 1 via the holding element 3 is moved to a desired position between two pedical screws 8, as likewise shown in FIG. 4.

Once the implant 7, which is connected to the guiding sleeve 1 and the holding element 3, has been moved to a desired position, the implant 7 can then be fixed in this position to the pedical screws 8. The screw connection between the holding element 3 and the implant 7 can then be released by rotating the holding element 3, i.e., the outer thread 4a on the front side of the holding element 3 is unscrewed from the inner thread 7a of the implant 7. The contact area between the guiding sleeve 1 and the implant 7 can include rotational blocking elements, such as for example protruding elements, which mesh with small grooves in the rear contact area of the implant 7, such that a tensile force on the holding element 3 firmly presses the implant 7 against the guiding sleeve 1 and the outer thread 4a of the holding element 3 can therefore be securely unscrewed from the implant 7, without thereby changing the position of the implant 7.

Once the connection between the holding element 3 and the implant 7 has been released, the holding element 3 can then be removed from the body together with the guiding sleeve 1, and the implant 7 has thus been navigated to a predetermined position using a minimally invasive method.

FIG. 5 shows a calibrating device 10 including three reflective markers 11a, 11b and 11c attached to it. Navigation markers and systems include those described in commonly assigned U.S. Pat. No. 6,351,659, which is incorporated herein by reference in its entirety. It is to be appreciated that the term "calibrate" is intended to mean determining the geometry or the spatial trajectory of a body generally, such as, for example, an instrument or element.

The upper side of the calibrating device 10 includes two faces 10a and 10d lying in a plane, between which two planes 10b and 10c form a generally V-shaped portion. A springelastic element 12 is attached on the upper side 10d. The element 12 can press onto the upper side of the calibrating element, which is lying on the calibrating device 10, in the direction indicated by the arrow F.

If the system shown in FIG. 3 is to be calibrated, i.e., the geometry of the system is to be ascertained, then the system can be placed in the slot or V-shape formed by the surfaces 10b and 10c and moved such that the system shown in FIG. 3 contacts at least one point on the surfaces 10b and 10c. If a number of rotational positions are detected, then the system can be calibrated on the basis of the position of the calibrating device 10 known using the markers 11a, 11b and 11c in combination with the position of at least one point on the system, shown in FIG. 3, known using the reference star 2. The elastic or spring-elastic element 12 can include a reflective marker 12a. The bias from the spring force pressing onto the surface of the instrument to be calibrated, which is inserted into the V-shape, can create another point of contact, which can be detected via the position of the marker 12a.

Therefore, the system shown in FIG. 3, or any instrument or element in general, can be calibrated.

It is to be appreciated that pre-operative or intra-operative planning can advantageously be performed for inserting the implant 7.

In the case of pre-operative planning, the position of different vertebrae can be detected using an imaging method, for example, MRI. The individual vertebrae can be segmented using a known method., i.e., the spatial boundary of each vertebra can be ascertained. On the basis of the detected (pathological) position, a surgeon can re-arrange the vertebrae until an optimum biomechanical position of the vertebrae with respect to each other is achieved. This can be performed using known simulation programs. It is then ascertained at which positions pedical screws of particular dimensions may advantageously be arranged. On the basis of this, it is possible to ascertain which shape an implant 7 to be inserted between the pedical screws 8 must have. The shape thus ascertained can then, for example, be printed out, such that the implant 7 can be shaped using the print-out as a model. Alternatively, it is also possible to select the implant suitable for a given case from a number of firmly predetermined implants.

In the case of intra-operative planning, the vertebrae to be treated can be segmented in a CT data set, (alternatively, this step can also be performed pre-operatively). Each vertebra can be individually registered and provided with a referencing device, such as, for example, a marker or an arrangement of markers, to enable all the registered vertebrae to be continuously tracked. If the spine is then re-shaped, for example, by shifting individual vertebrae, the new shape (the relative position of the vertebrae to each other) can be displayed on the screen and compared, for example, with a pre-operatively or even intra-operatively planned shape. Using the now known current shape and the already planned pedical screws, the shape of an implant to be inserted, such as, for example, a connecting rod, can then be calculated.

The thus selected or shaped implant 7 can then be connected to the guiding sleeve 1 and the holding element 3, as shown in FIGS. 1 to 3.

The system consisting of the guiding sleeve 1, holding element 3 and implant 7 can be calibrated using the calibrating device 10, shown in FIG. 5.

The implant can then be navigated in a minimally invasive way to the position ascertained by pre-operative planning, and held in this position once it has been fixed to the pedical screws, while at the same time the holding element 3 and the guiding sleeve 1 are released from the implant 7, such that the implant 7 can be navigated to a desired position in a minimally invasive way.

Although particular embodiments of the invention have been described in detail, it is understood that the invention is not limited correspondingly in scope, but includes all changes, modifications and equivalents coming within the spirit and terms of the claims appended hereto.

What is claimed is:

1. A system for positioning an implant, said system comprising:
    a holding element for holding an implant, said holding element including:
        a first end having a grip,
        a second end having a connecting element for establishing a connection to the implant, and
        an elongated intermediate portion extending between the first and second ends; and
    a guiding sleeve for guiding the holding element, said guiding sleeve having an entry opening and an exit opening, and defining a guiding area between the openings for guiding the elongated intermediate portion of the holding element, wherein the holding element is removably introduceable into the guiding sleeve, wherein the holding element is configured to be translated within the guiding sleeve, wherein a tensioning device is provided proximate the first end, the tensioning device being configured to move axially the holding element after an implant has been connected to the second end of the holding element so as to move the implant into abutment with an adjacent end of the guiding sleeve and place the elongated intermediate portion under tension; and wherein the tensioning device includes a nut that is screwed onto the holding element, which nut is operable to engage an adjacent end of the guiding sleeve opposite the end that is engaged by the implant.

2. The system as set forth in claim 1, wherein the guiding sleeve is made of a rigid material.

3. The system as set forth in claim 1, wherein the guiding sleeve includes at least one curved section.

4. The system as set forth in claim 1, further comprising a navigation element fixed to the guiding sleeve, the navigation element having markers specifically designed to be trackable by a navigation system.

5. The system as set forth in claim 1, further comprising a sliding element connected to a navigation element, said sliding element slidably engaging the guiding sleeve.

6. The system as set forth in claim 1, wherein one end of the guiding sleeve includes an end area which tapers conically outward or inward.

7. The system as set forth in claim 6, wherein the guiding sleeve includes a rotational block at the conically tapered end area.

8. The system as set forth in claim 1, wherein the connecting element of the holding element comprises an outer thread.

9. The system as set forth in claim 8, wherein the holding element includes a flexible area which can be guided in the guiding sleeve.

10. The system as set forth in claim 8, further comprising the implant that includes a connecting element for establishing a connection to the connecting element of the holding element.

11. The system as set forth in claim 10, wherein the connecting element of the implant is an inner thread.

12. The system as set forth in claim 10, wherein the implant includes a conically tapered section adjacent the connecting element.

* * * * *